(12) United States Patent  (10) Patent No.: US 9,333,342 B2
Haasl et al.  (45) Date of Patent: May 10, 2016

(54) SYSTEM AND METHODS FOR CHRONIC FIXATION OF MEDICAL DEVICES

(71) Applicant: Cardiac Pacemakers, Inc., St. Paul, MN (US)

(72) Inventors: Benjamin J. Haasl, Forest Lake, MN (US); Brian L. Schmidt, White Bear Lake, MN (US); Arthur J. Foster, Blaine, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 0 days.

(21) Appl. No.: 14/336,694

(22) Filed: Jul. 21, 2014

(65) Prior Publication Data

US 2015/0025612 A1  Jan. 22, 2015

Related U.S. Application Data

(60) Provisional application No. 61/857,109, filed on Jul. 22, 2013.

(51) Int. Cl.
*A61N 1/05* (2006.01)

(52) U.S. Cl.
CPC .............. *A61N 1/0573* (2013.01); *A61N 1/056* (2013.01); *A61N 1/059* (2013.01)

(58) Field of Classification Search
CPC ...... A61N 1/057; A61N 1/0573; A61N 1/059
USPC ............ 607/119, 126–128, 130, 131
See application file for complete search history.

(56) References Cited

U.S. PATENT DOCUMENTS

| | | | |
|---|---|---|---|
| 5,545,201 A | 8/1996 | Helland et al. | |
| 7,212,870 B1 | 5/2007 | Helland | |
| 7,532,933 B2 | 5/2009 | Hastings et al. | |
| 2004/0116992 A1* | 6/2004 | Wardle | A61B 5/0215 607/116 |
| 2005/0065589 A1* | 3/2005 | Schneider | A61B 17/0057 607/126 |
| 2006/0085042 A1* | 4/2006 | Hastings | A61N 1/0587 607/33 |
| 2007/0100411 A1* | 5/2007 | Bonde | A61N 1/0558 607/126 |
| 2007/0135883 A1* | 6/2007 | Drasler | A61B 5/6848 607/126 |
| 2007/0239248 A1* | 10/2007 | Hastings | A61N 1/0573 607/127 |
| 2008/0082132 A1* | 4/2008 | Annest | A61F 2/2487 607/4 |
| 2009/0082828 A1 | 3/2009 | Ostroff | |
| 2010/0198288 A1 | 8/2010 | Ostroff | |
| 2010/0256696 A1* | 10/2010 | Schleicher | A61N 1/0558 607/2 |
| 2012/0116489 A1 | 5/2012 | Khairkhahan et al. | |
| 2012/0158111 A1 | 6/2012 | Khairkhahan et al. | |

* cited by examiner

*Primary Examiner* — Allen Porter, Jr.

(74) *Attorney, Agent, or Firm* — Seager, Tufte & Wickhem LLP (57) ABSTRACT

Devices or methods such as for stimulating excitable tissue or sensing physiologic response or other signals that can use chronic fixation mechanism are described. An implantable electrostimulation apparatus can comprise an electrostimulation electrode assembly that can include a primary fixation member and a secondary fixation member. The primary fixation member can be actively engaged or affixed to a target tissue of a patient, and the second fixation member can be biased against the target tissue, collapsed or compressed against the target tissue when the primary fixation member is affixed to the target tissue. The electrostimulation electrode assembly can also include at least one electrode such as to contact heart or other excitable tissue such as to deliver chronic electrostimulation or sensing physiologic responses.

18 Claims, 5 Drawing Sheets

SYSTEM AND METHODS FOR CHRONIC FIXATION OF MEDICAL DEVICES

CLAIM OF PRIORITY

This application claims the benefit of priority under 35 U.S.C. §119(e) of U.S. Provisional Patent Application Ser. No. 61/857,109, filed on Jul. 22, 2013, which is herein incorporated by reference in its entirety.

TECHNICAL FIELD

This document relates generally to medical devices, and more particularly, to devices and methods for affixing the medical devices to target tissue and stimulating excitable tissue or sensing physiologic response.

BACKGROUND

Ambulatory medical devices, such as implantable pacemakers and cardioverter-defibrillators, can chronically stimulate excitable tissues or organs, such as a heart, such as to treat abnormal cardiac rhythms such as bradycardia or tachycardia, or to help improve cardiac performance such as by correcting cardiac dyssynchrony in a patient with congestive heart failure (CHF). Such ambulatory medical devices can have one or more electrodes that can be positioned within the heart or on a surface of the heart for contacting the cardiac tissue. The electrodes can be electrically coupled to an electronics unit such as a pulse generator and can be used to deliver one or more electrostimulations to the heart, such as to help improve heart function.

OVERVIEW

Cardiac stimulation using an implantable medical device (IMD) can involve one or more implantable leads that can be transvascularly inserted into one of the heart chambers, such as an atrium or a ventricle. Stimulation of the heart can be accomplished through direct myocardium stimulation using one or more electrodes that are electrically connected to the IMD and in close contact with the cardiac tissue. The electrodes can be positioned along the one or more implantable leads, or directly attached to an IMD without a lead. The stimulation is provided at specified stimulation strength (e.g., stimulation energy) sufficient to capture the heart, resulting in an evoked electrical depolarization and mechanical contraction.

The one or more electrodes (with or without a lead) can be placed inside a heart chamber, or on a surface of the heart. Electrostimulation using one or more electrodes affixed on the heart surface such as for epicardial stimulation may benefit some patients, including children or persons with a compromised venous system. To enable reliable delivery of chronic stimulation therapy, the implantable leads must be securely affixed to the stimulation site. One way of fixation is through passive fixation such as by using tines attached to the lead to allow the lead to snag and get embedded in, for example, the trabeculae in the interior surface of the ventricles. Fixation can also include active fixation such as by using screws that can penetrate and tightly engage with the heart tissue.

While passive fixation is usually used where there exist abundant trabeculae at or around the fixation site, active fixation can be more effective at the fixation site lacking the trabecular tissue. However, active fixation can cause tissue trauma. Particularly, for epicardial stimulation, there are tissues on the heart surface that can be more prone to trauma or severance damage, such as coronary arteries or nerve tissues. To avoid or reduce trauma to these vulnerable tissues during lead or electrode fixation, smaller fixation element is more desirable because it can reduce tissue trauma and can provide higher current density to the tissue, thereby reducing stimulation threshold for achieving effective myocardial stimulation.

However, as lead body and fixation element gets smaller, the fixation element can be more prone to dislodgement. For example, screw-in active fixation lead works only when there is neutral or no counter rotational forces. Reduced torsional stiffness associated with the smaller fixation element would more likely cause the fixation element to back out of the tissue and detach from the fixation site such as due to heart beat, patient movement, or daily activities over time. The lead dislodgement may result in an increase in pacing thresholds, failure to sense, extra cardiac stimulation, loss of pacing therapy, deteriorated heart failure (such as in patient requiring biventricular resynchronization pacing), inappropriate therapies by automatic defibrillators, syncope, among others. The dislodged lead can perforate into neighboring tissue and cause infection, or migrate out of the heart and lodge in other tissue or organs (such as lungs) and cause thromboembolic complications or other serious outcome. Management of dislodged cardiac pacing leads typically requires reoperation to reposition the lead. Thus, the present inventors have recognized that there remains a considerable need for better devices and methods such as for improving the reliability of chronic fixation of the IMD and the consistency of chronic stimulation therapy.

Various embodiments described herein can help improve electrical cardiac stimulation or can reduce the chance or lead dislodgment. For example, an implantable apparatus can comprise an electrostimulation electrode assembly. The electrostimulation electrode assembly can include a primary fixation member, a secondary fixation member, and an electrostimulation electrode body. The primary fixation member can be sized, shaped, or otherwise configured to be actively engaged or affixed to a target tissue of a patient. The second fixation member can be sized, shaped, or otherwise configured to bias against the target tissue when the primary fixation member is engaged or affixed to the target tissue. An example of the second fixation member can be compressible and configured to be collapsed or compressed against the target tissue in response to the primary fixation member being affixed to the target tissue. The electrostimulation electrode body can be configured to be attached to the primary fixation member and the secondary fixation member. The electrostimulation body can include at least one electrode which can be configured to deliver electrostimulation to the target tissue.

An implantable medical device (IMD) embodiment can comprise an electrostimulation unit configured to provide electrostimulation to a heart to achieve desirable therapeutic or diagnostic effects. The IMD can include a primary fixation member sized, shaped, or otherwise configured to be actively engaged or affixed to the heart. The IMD can include a secondary fixation member sized, shaped, or otherwise configured to be collapsed and compressed to bias against, and without being actively engaged or affixed to, the heart when the primary fixation member is engaged or affixed to the heart. The electrostimulation unit can be configured to be attached to the primary fixation member and the secondary fixation member, and to deliver electrostimulation to a stimulation site of the heart via at least one electrode, when at least one of the primary or the secondary fixation member is affixed to the heart.

A method example can include providing an implantable medical device (IMD) configured to deliver an electrostimulation to a stimulation site of a patient. The IMD can be provided with a primary fixation member configured to be actively engaged or affixed to a target tissue, and a secondary fixation member configured to be collapsed or compressed against the target tissue when the primary fixation member is engaged or affixed to the target tissue. The method includes providing the IMD that can be engaged or affixed to the target tissue by using at least one of the primary and secondary fixation members, and delivering the electrostimulation to the stimulation site via at least one electrode.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are apparatuses and methods for stimulating a target tissue of a heart or other excitable tissues of a patient, such as to achieve desired diagnostic or therapeutic effect. The target tissue can include an epicardial or endocardial site. The stimulation apparatus can include one or more electrostimulation electrodes that can be affixed to the target tissue such as a heart tissue using at least one of a primary and a secondary fixation member. The apparatus and the methods described herein can also be applicable to stimulation or sensing of other tissues or organs in the body.

Figure 1:
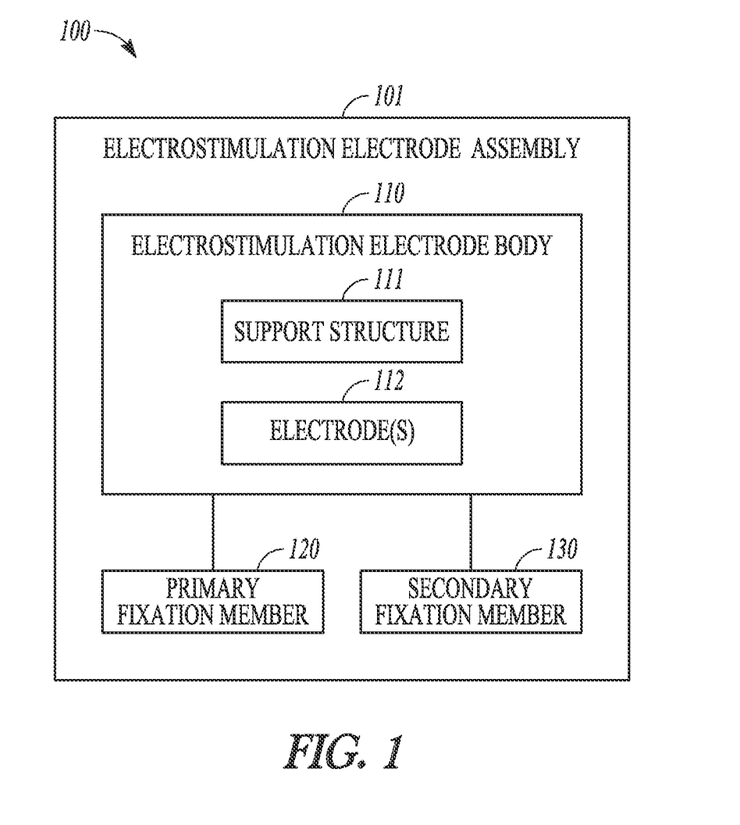
FIG. 1 illustrates an example of an implantable apparatus comprising a modular electrostimulation electrode assembly.

FIG. 1 illustrates a schematic example of an implantable apparatus 100 that can include an electrostimulation electrode assembly 101. The electrostimulation electrode assembly 101 can be configured to be chronically affixed to a location of a heart such as on the surface of the heart or inside a heart chamber such as an atrium or a ventricle, and to provide chronic stimulation to heart to achieve desirable diagnostic or therapeutic effects. The electrostimulation electrode assembly 101 can be configured to be affixed to other tissue or organ and to stimulation the tissue or organ therein. Examples of such organs or tissues can include an interior or exterior of an artery or vein, a nerve bundle, skin, a carotid body, a stomach or intestine, a bladder, a kidney, soft tissue, gastric tissue, or neural tissue.

The modular electrostimulation electrode assembly 101 can include an electrostimulation electrode body 110, a primary fixation member 120, and a secondary fixation element 130. The primary fixation member 120 and the secondary fixation member 130 can be attached or coupled to the electrostimulation electrode body 110. The electrostimulation electrode body 110 can include a support structure 111 and one or more electrodes 112. The support structure 111 can be sized, shaped, or otherwise configured to be positioned to the stimulation site such as on the surface of the heart, inside a heart chamber, within a blood vessel, within subcutaneous tissue, or at other locations in the body of a patient. In some examples, the support structure 111 can be configured to be chronically implanted in the heart or other tissues or organs. The support structure 111 can be configured to hold the electrodes 112 and facilitate the positioning of the electrode 112 to the desired stimulation site, and to deliver the electrostimulation thereto or therein.

In an example, the electrostimulation electrode body 110 can be a part of a stimulation delivery system such as a lead, a catheter, or other stimulation delivery device. The support structure 111 can include a distal end, a proximal end, and an elongated member between the distal and the proximal ends. The one or more electrodes 112 can be individually addressable such that each electrode can be electrically connected to a stimulator such as via separate conductors that can be mutually insulated from each other. The conductors can be encapsulated within and extended longitudinally along the elongated member of the support structure 110. The electrodes 112 can be positioned at one end of the support structure, such as the distal end, or anywhere along the elongated member of the support structure 111.

The electrostimulation electrode assembly 101 can be configured to couple to a stimulator such as through the proximal end of the support structure 111. Examples of the stimulator can include an ambulatory medical device including an implantable pacemaker, an implantable defibrillator, an implantable cardiac resynchronization therapy (CRT) stimulator, a neural stimulator, an external pacing system analyzer (PSA) circuit, or other implantable, wearable, or bedside electrostimulation generators. In an example, the stimulator can be separate from or external to the electrostimulation electrode assembly 101. In an example, the electrostimulation electrode assembly 101 can be configured to use electrode 112 to sense a biopotential signal such as from the heart, or other physiological signals from the contacting or surrounding tissue. The stimulator can include circuitry or a processing unit configured to process the sensed biopotential or physiological signals and generate information indicative of patient diagnostics or therapy efficacy.

The electrostimulation electrode body 110 can include an untethered electrostimulator device such as an implantable electrostimulator, which need not be tethered to another device by a leadwire or other wired connection. The support structure 111 can serve as housing or a "can" of the untethered ambulatory medical device within which it carries or houses the electrostimulation generation circuit or one or more other electrical components of the stimulator. The electrostimulation generation circuit can be configured to generate and deliver electrostimulation to the target tissue. Examples of the untethered electrostimulator device are discussed below, such as with reference to FIGS. 4A-B.

The primary fixation member 120 can be sized, shaped, or otherwise configured to engage with a target tissue. As illustrated in FIG. 1, the primary fixation member 120 can be attached to the electrostimulation electrode body 110, which allows the electrostimulation electrode assembly 101 to be securely affixed to a target site of the tissue or organ to be stimulated. In an example where the electrostimulation electrode body 110 includes an electrostimulation lead, the primary fixation member 120 can be mounted on the distal end of the electrostimulation lead. In another example where the electrostimulation electrode body 110 includes an untethered electrostimulator device, the primary fixation member 120 can be mounted on an exterior surface of the untethered electrostimulator device.

The primary fixation member 120 can include a passive fixation mechanism, an active fixation mechanism, or a combination of one or more passive or active fixation mechanisms. Examples of the passive fixation can include one or more tines, one or more fins, one or more helices, or one or more other extension structures. Examples of the active fixation can include one or more screws, one or more hooks, one or more barbs, one or more helices, or one or more other tissue-penetrating mechanisms. In an example, the primary fixation member 120 can include a rotationally-oriented element, such as a helical coil or a spiral coil. The primary fixation member 120 can include a tapered end on the rotationally-oriented element to facilitate active engagement with the target tissue, such as a screw-in helical coil. The primary fixation member 120 can be made out of biocompatible materials with desired stiffness, such as stainless steel, titanium alloy, polymer, ceramic, or other synthetic biocompatible metallic or non-metallic materials.

The secondary fixation member 130 can be attached to the electrostimulation electrode body 110, such as on the distal end of an electrostimulation lead or on an exterior surface of an untethered electrostimulator device. The secondary fixation member can assist the primary fixation member 120 in securing the electrostimulation electrode assembly 101 on the target tissue and preventing the electrostimulation electrode assembly 101 from dislodging from the target tissue such as due to the backing, loosening, unwinding or unscrewing of the primary fixation member 120 such as due to heart beat, patient motion or movement, and other daily activities. For example, the secondary fixation member 130 can be sized, shaped, or otherwise configured to bias against the target tissue when the primary fixation member is engaged or affixed to the target tissue. In various examples, the secondary fixation member 130 can include a compressible structure including a helix, a coil, a spring, a sponge, or other biocompatible synthetic compressible materials. By using the compressible structure or a compressible material, at least a portion of the secondary fixation member 130 can be configured to be collapsed and compressed against the target tissue when the primary fixation member 120 is engaged or affixed to the target tissue. The compressed or collapsed secondary fixation member can exert increased tension between the electrostimulation electrode body 110 and the target tissue engaged by the primary fixation member 120, thereby reducing the likelihood of the primary fixation member 120 and thus the electrostimulation electrode body 110 from detaching from the target tissue.

In various examples, at least one of the primary fixation member 120 or the secondary fixation member 130 can include a suture retention feature which can allow for or facilitate suturing the electrostimulation assembly 101 to the target tissue. In another example, at least a portion of at least one of the primary fixation member 120 or the secondary fixation member 130 can be textured or porous, such as on a scale that can be configured to permit or facilitate tissue ingrowth. For example, the fibrotic tissue that can be formed around the primary fixation member 120 or the secondary fixation member 130 can help more firmly hold the electrostimulation electrode body 110 against the target tissue. In an example, at least a portion of at least one of the primary fixation member 120 or the secondary fixation member 130 can include an attachment or a coating of porous biomaterial or porous synthesized material that allows for or promote tissue ingrowth. Examples of the porous material can include one or more of titanium or stainless steel fiber mesh, porous tantalum, or polyester or heavyweight polypropylene mesh, among others.

Figure 2A:
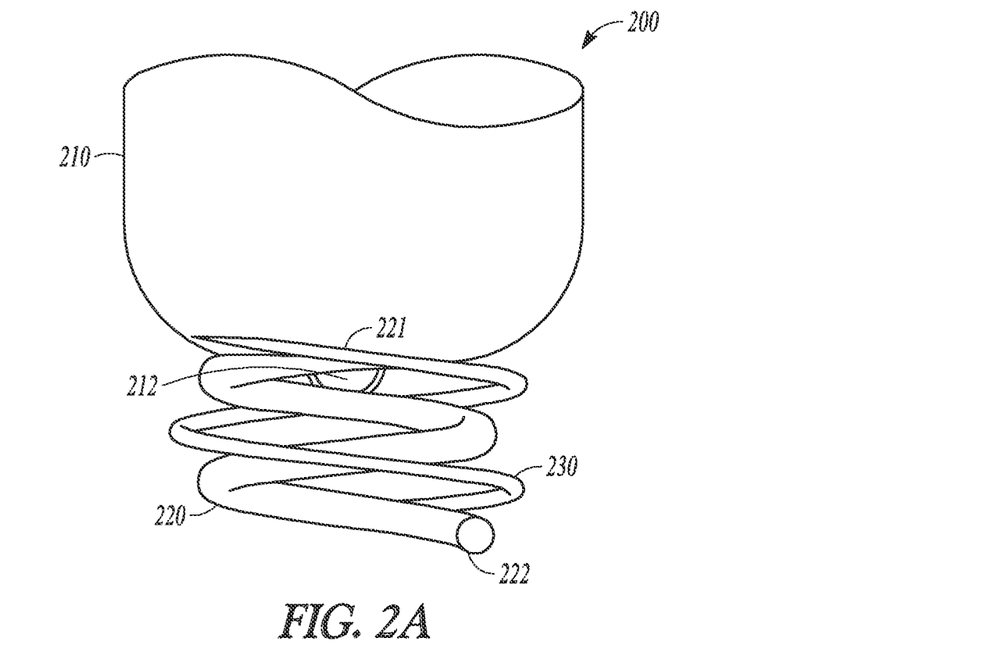
FIGS. 2A-B illustrate examples of an implantable electrostimulation electrode assembly.
Figure 2B:
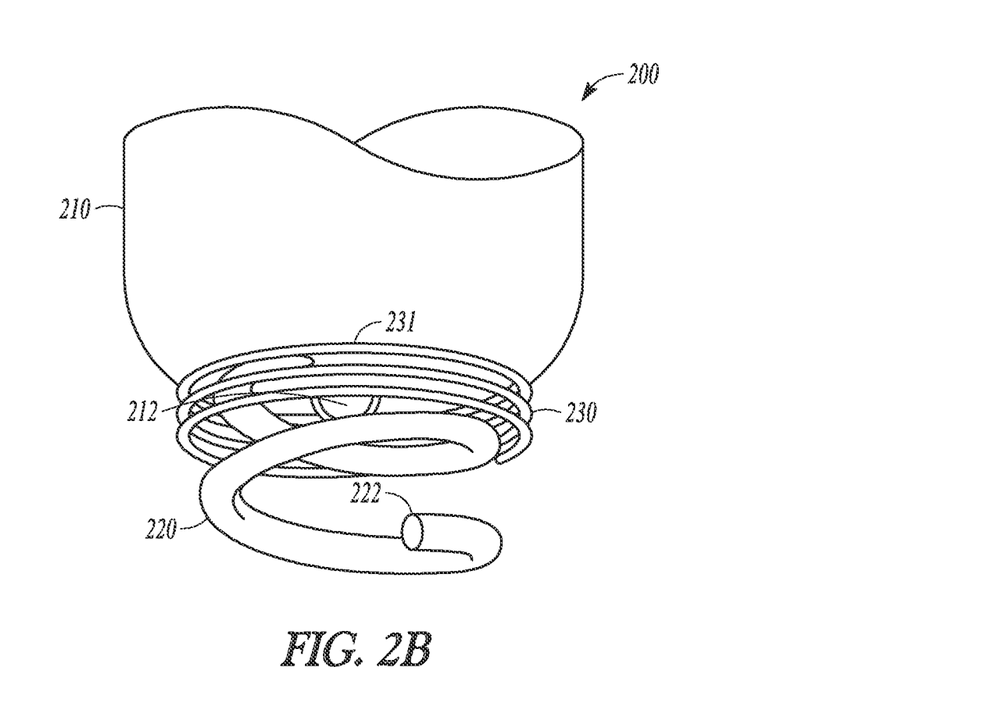

FIGS. 2A-B illustrate examples of an implantable electrostimulation electrode assembly 200, which can be an embodiment of the electrostimulation electrode assembly 101. The implantable electrostimulation electrode assembly 200 can include an electrostimulation electrode body 210, a primary fixation member 220, and a secondary fixation member 230. FIG. 2A illustrates an example of the primary and secondary fixation embers in their respective disengaged state (i.e., without engaging with the target tissue), and FIG. 2B illustrates an example of the primary and the secondary fixation members 230 in their respective engaged state (i.e., when engaging with the target tissue).

The electrostimulation electrode body 210 can be configured to be attached to the primary fixation member 220 and a secondary fixation member 230. The electrostimulation electrode body 210 can include one or more electrodes, such as electrode 212, for delivering electrostimulation to a stimulation site. In an example, the electrostimulation electrode body 210 can have a longitudinal shape extending between a proximal end and a distal end.

The primary fixation member 220 can be positioned on an exterior of the electrostimulation electrode body 210, such as protruding from a distal end of the electrostimulation electrode body 210. The primary fixation member 220 can includes an active fixation helical or spiral coil body extending rotationally between a distal end 222 and a proximal end 221. The proximal end 221 can be attached to the electrostimulation electrode body 210, and the distal end 222 of the primary fixation member 220 can include a hook, a barb, a screw-in element, or other tapered element to facilitate tissue penetration and fixation. The helical coil body can have a uniform diameter. In an example, the primary fixation member 220 can includes a spiral coil body with one of gradually increasing diameters, gradually decreasing diameters, or other spiral shapes.

The secondary fixation member 230 can include a helical or spiral coil rotationally extending between a proximal end 231 and a distal end 232. The secondary fixation member 230 can be attached to an exterior of the electrostimulation electrode body 210 such as via the proximal end 221 at a location within a close proximity to the primary fixation member 220.

The secondary fixation member 230 can be sized, shaped, or configured such that at least a portion of the secondary fixation member 230 can be compressed against the target tissue when the primary fixation member 220 is engaged with or affixed to the target tissue. As illustrated in FIGS. 2A-B, the helical or spiral coil of the secondary fixation member 230 and the helical or spiral coil of primary fixation member 220 can be coaxial, and both the primary and secondary fixation members can axially align with the electrostimulation electrode body 210. Being coaxial with the primary active fixation member 220 can allow the compression force to be evenly distributed across the secondary fixation member 230 and to be evenly distributed to the tissue engaged with the primary fixation member 220, thereby tightly securing the primary fixation member 220 on the target tissue.

Several features of the secondary fixation member 230 have been contemplated to facilitate its collapse or compression against the target tissue when the primary fixation member 220 is engaged or affixed to the target tissue. In one example, the spiral or helical coil of the secondary fixation member 230 can have a different pitch than that of the spiral or helical coil of the primary fixation member 220. A pitch of a helix or spiral is the width of one complete helix turn measured from the center of the helix or spiral. The secondary fixation member 230 can have, for example, a lower pitch than the primary fixation member 220 to achieve an elasticity that provides desirable compression force exerted against the target tissue.

In some cases, the spiral or helical coil of the secondary fixation member 230 can have a reversed handedness than that of the spiral or helical coil of the primary fixation member 220. That is, the secondary fixation element 230 can be counter-wound relative to the primary fixation element 220. For example, the secondary fixation member 230 can have left handedness winding if the primary fixation member 220 has a right handedness winding, or the secondary fixation member 230 can have a right handedness winding if the primary fixation member 220 has a left handedness winding. The opposite handedness can allow the secondary fixation member 230 to be effectively compressed between the electrostimulation electrode body 210 and the target tissue without penetrating or damaging the tissue, when the primary fixation member 220 is being actively screwed into the tissue. Additionally, the opposite handedness can also offer an anti-unscrewing feature. For example, if the primary fixation member 220 tend to unscrew out of the tissue such as due to heart beat or patient activity, the reversely-wound secondary fixation member 230 can exert resistance to the otherwise rotational unscrewing, thereby preventing the electrostimulation electrode body 210 from turning or reorienting itself and dislodging from the target tissue.

The distal end 232 of the secondary fixation member can be blunt, bulged, or otherwise sized, shaped, or configured to increase the resistance against the un-screwing effect. In an example, at least a portion of the secondary fixation element 230 such as at or near the distal end 232 can be textured or porous, or can be attached to or coated with a porous biomaterial or a porous synthesized material such as to promote tissue ingrowth.

At least a portion of the secondary fixation member 230 can include one or more of stainless steel, titanium alloy, plastic, polyurethane or other types of polymer, ceramic, other synthetic biocompatible metallic or non-metallic materials, or a combination of two or more materials such as plastic-coated metal, or multifilar windings around the flexible metallic core. The secondary fixation member 230 can be made out of a material with different stiffness than the primary fixation member 220. For example, the primary fixation member 220 can be made out of a material stiffer than the secondary fixation member 230. In an example, the secondary fixation member 230 can be made with metal wire with lower tensile than that used for the helical coil of the primary fixation element 220.

The secondary fixation member 230 can include various geometric features to promote the collapse or compression against the target tissue in response to the primary fixation member 220 being affixing to the target tissue. For example, the coaxial primary and secondary fixation members can have different diameters, such that the two helical or spiral coils of the first and secondary fixation members can form a double-helix or double-spiral configuration with an inner helical or spiral coil having a smaller diameter and the an outer helical or spiral coil having a larger diameter. In one example, the inner helical or spiral coil can constitute a part of the primary fixation member 220, and the outer helical or spiral coil can constitute a part of the secondary fixation member 230. In another example, the inner helical or spiral coil can constitute a part of the secondary fixation member 230, and the outer helical or spiral coil can constitute a part of the primary fixation member 220. A primary fixation member 220 with a smaller diameter can reduce the trauma caused by active fixation; and a helical coil of the secondary fixation member 230 with a larger diameter can provide stronger compression forces against the target tissue and thus improved anti-unscrewing capability when the primary fixation member 220 is affixed to the target tissue. In other examples, the helical or spiral coils of the primary and the secondary fixation members can have the same parameter.

The helical or spiral coil of the primary fixation member 220 can extend farther from the electrostimulation electrode body 210 than the helical or spiral coil of the secondary fixation member 230. A longer coil length of the primary fixation member 220 can allow at least a portion of the coil body of the primary fixation member 220 to be actively affixed to the target tissue without the secondary fixation member being compressed, thereby reducing the resistance exerted by the secondary fixation member 230 while the primary fixation member 220 is being affixed to the target tissue.

In various examples, at least a portion of the secondary fixation member 230 can include radiopaque material which can provide a radiopaque reading of a degree of fixation of the electrostimulation electrode assembly 201 to the target tissue. For example, particularly when the secondary fixation member 230 is made out of non-metallic materials such as polymers, at least a portion of the secondary fixation member 230 can be coated with dense metal powders and compounds including one or more of barium, barium sulfate, tungsten, bismuth compounds, among other substances opaque to x-rays. The radiopaque coating can be applied to specified area according to a specified pattern on the surface of the secondary fixation member 230. When the secondary fixation member 230 is compressed, the degree of deformation can be readily visible under fluoroscopy or x-ray imaging. The image can be presented to and end user such as a physician to determine if the electrostimulation electrode assembly 201 has been desirably affixed to the target tissue. In some examples, at least a portion of each of the primary fixation element 220 and the secondary fixation element 230 can be coated with radiopaque materials, and a desirable fixation of the electrostimulation electrode assembly 201 can be determined using the degree of engagement of the primary fixation member 220 with the target tissue, the degree of compression of the secondary fixation member 230 against the target tissue, or both.

The electrode 212 can deliver electrostimulation to the stimulation site. The electrode 212 can be sized and shaped to allow for close contact with the tissue at the stimulation site when the implantable electrostimulation electrode assembly 200 is implanted. In an example, the electrode 212 can be a button-shape electrode. The electrode 212 can be disposed at the distal end of the electrostimulation electrode body 210, as illustrated in FIGS. 2A-B. The electrode 212 can be concentric with one or both of the primary fixation member 220 and the secondary fixation member 230, such that the electrode 212 can closely contact the stimulation tissue when the primary fixation member 220 or the secondary fixation member 230 are engaged with the tissue, and can provide less trauma to the tissue to be stimulated.

In some examples, at least one of the primary fixation member 220 or the second fixation member 230 can be electrically "active" such as being electrically coupled to an electrostimulation generation circuit. The electrostimulation generation circuit, either separated from or included in the electrostimulation electrode assembly 201, can be configured to generate and deliver the electrostimulation to the stimulation site via at least one of the primary fixation member 220 or the second fixation member 230. In other examples, at least one of the primary fixation member 220 or the second fixation member 230 can be configured to be electrically inactive such as not being coupled to the electrostimulation circuit or providing electrostimulation to the tissue. The electrostimulation circuit can generate and deliver electrostimulation to the target tissue through one or more separate electrodes at or along the surface of the electrostimulation electrode body 210. In a specific embodiment, while the primary fixation element 220 can be electrically active, the secondary fixation element can be configured to be electrically inactive.

Figure 3A:
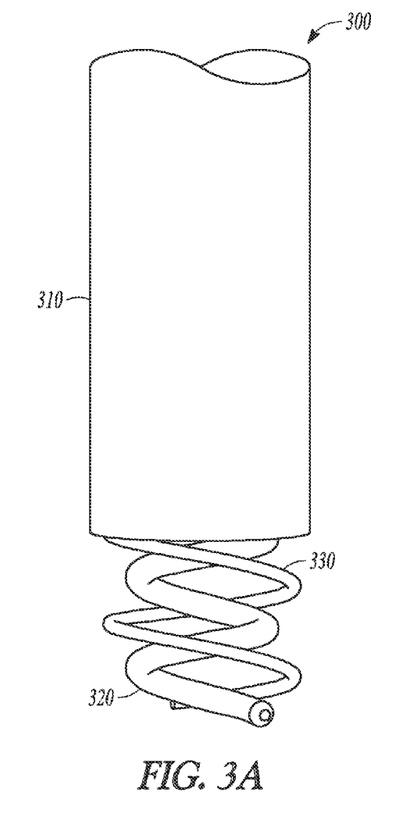
FIGS. 3A-B illustrate examples of an implantable medical device for delivering electrostimulation.
Figure 3B:
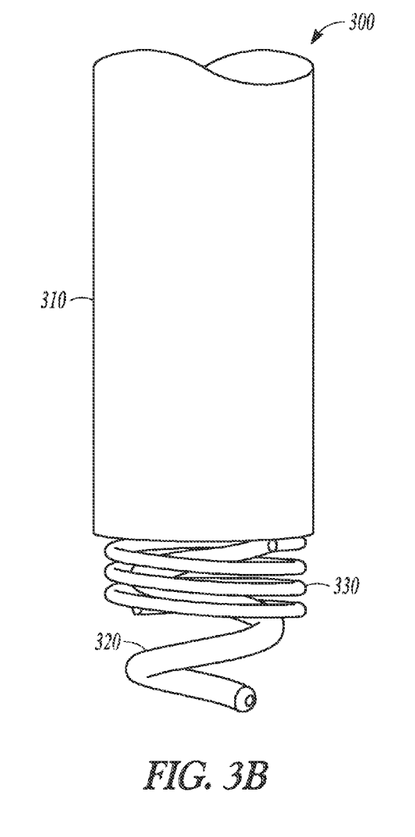

FIGS. 3A-B illustrate examples of an implantable medical device 300 for delivering electrostimulation to a target tissue in a patient. The implantable medical device 300 can be an example of the electrostimulation electrode assembly 201. The implantable device 300 can be configured to deliver electrostimulation to an interior of a heart chamber (such as an atrium or a ventricle) or heart surface such as an epicardium. The implantable device 300 can be configured to deliver electrostimulation to other tissues or organs including an interior or exterior of an artery or vein, a nerve bundle or other neural tissue, skin, a carotid body, a stomach or intestine, a bladder, a kidney, soft tissue, or gastric tissue.

As illustrated in FIGS. 3A-B, the medical device 300 can include an electrostimulation unit 310, a primary fixation member 320, and a secondary fixation member 330. FIG. 3A illustrates an example when the primary fixation and the secondary fixation members are in their respective disengaged state (i.e., without engaging with the target tissue), and FIG. 3B illustrates an example when the primary and the secondary fixation members 320 are at least partially engaged with the heart tissue.

The electrostimulation unit 310 can be shaped, sized, or otherwise configured for approaching the heart surface such as through a sub-xiphoid approach, or for approaching the interior of the heart chamber such as through a transvenous approach. The electrostimulation unit 310 can comprise an at least partially elongated body such as a wire, a lead, or a catheter that extends between a distal end and a proximal end. In some examples, the electrostimulation unit 310 can include one or more electrodes to deliver electrostimulation to the desired stimulation site of the heart. The at least one electrode can be electrically coupled to a separate electrostimulation generator such as via the proximal end of the electrostimulation unit 310. Examples of the electrostimulator generator can include an implantable pacemaker, an implantable defibrillator, an implantable cardiac resynchronization therapy (CRT) stimulator, a neural stimulator, an external pacing system analyzer (PSA) circuit, or other implantable, wearable, or bedside electrostimulation generators.

The one or more electrodes can be position on, for example, the distal end of the electrostimulation unit 310, or anywhere along the exterior surface of the electrostimulation unit 310. In some examples, the at least one electrode is configured to deliver the electrostimulation to the stimulation site on or within the heart only when at least one of the primary fixation member 320 or the secondary fixation member 330 is engaged with the heart tissue. In some embodiments, the electrodes can be configured to sense one or more physiological signals from the heart, and the electrostimulator generator can include circuit configured to process the sensed physiological signals to provide the processed diagnostic information to a healthcare provider such as a physician.

The primary fixation member 320 can be sized, shaped, or otherwise configured to be affixed to or engaged with the heart. As illustrated in FIGS. 3A-B, the primary fixation member 320 can include a screw-in helical coil securely attached to a distal end of the electrostimulation unit 310. The primary fixation member 320 can have a tapered distal end extending distally from the helical coil to facilitate penetration and active fixation to the heart.

The secondary fixation member 330 can be sized, shaped, or otherwise configured to be collapsed and compressed to bias against the desired stimulation site of the heart when the primary fixation member 320 is engaged or affixed to the heart. In an example, as illustrated in FIGS. 3A-B, the secondary fixation member 330 can include a helical coil coaxial with the primary fixation member 320, but exclude an active fixation element. Both the primary and secondary fixation members can axially align with the electrostimulation unit 310. The diameter of the secondary fixation member 330 can be larger than the primary fixation member 320. A smaller-sized primary fixation member 320 can reduce the trauma caused by active fixation; while a relatively larger secondary fixation member 330 can provide stronger compression forces against the target tissue and more robust anti-unscrewing capability when the primary fixation member 320 is affixed to the target tissue. To facilitate the compression, in some examples, the secondary fixation member 330 can be made out of material more pliable than that for the primary fixation member, including one or more of stainless steel, titanium alloy, plastic, polyurethane or other types of polymer, ceramic, other synthetic biocompatible metallic or non-metallic materials, or a combination of two or more materials such as plastic-coated metal, or multifilar windings around the flexible metallic core. The helical coil of the secondary fixation member 330 can have a lower pitch than the primary fixation member 320.

In some examples, the helical coil of the secondary fixation member 330 can have opposite handedness than the primary fixation member 320. The opposite handedness can allow the secondary fixation member 330 to be effectively compressed against the target tissue without actively penetrating or damaging the target tissue when the primary fixation member 220 is being actively screwed into the tissue. Additionally, the opposite handedness can allow the secondary fixation member 330 to exert resistance against the rotational unscrewing of the active fixation of the primary fixation member 320 such as due to heart beat or patient activity.

The primary fixation member 320 can have a longer length extended distally from the electrostimulation unit 310 than the secondary fixation member 330, such that at least a portion of the primary fixation member 320 can be actively affixed to the target tissue without the secondary fixation member 330 being compressed. In some examples, the secondary fixation member 330 can be configured to be compressed against the electrostimulation unit 310 such as by using a user-controllable stopper element that prevents the secondary fixation member 330 from contacting the target tissue unless and until the primary fixation member 320 has achieved desirable fixation to the target tissue; and by then the stopper element can be disengaged and the secondary fixation member 330 can be released and expanded between the electrostimulation unit 310 and the target tissue, and contact and compress against the target tissue. In some examples, the secondary fixation member can include radiopaque material such that the secondary fixation member 330 can be capable of providing a radiopaque reading of a degree of fixation of the electrostimulation electrode assembly.

One or both of the primary fixation member 320 or the secondary fixation member 330 can be electrically coupled to the electrostimulation generator (such as an ambulatory medical device or a PSA circuit) and deliver the electrostimulation to the heart or other target tissue. The electrostimulator generator can be configured to deliver a unipolar stimulation or a bipolar stimulation. The unipolar stimulation can be provided such as using the primary fixation element 320 and a return electrode such as the "can" or housing of an ambulatory medical device. The bi-polar stimulation can be provided such as between the primary fixation element 320 and the secondary fixation element 330 or other separate electrode on the electrostimulation unit 310.

Figure 4A:
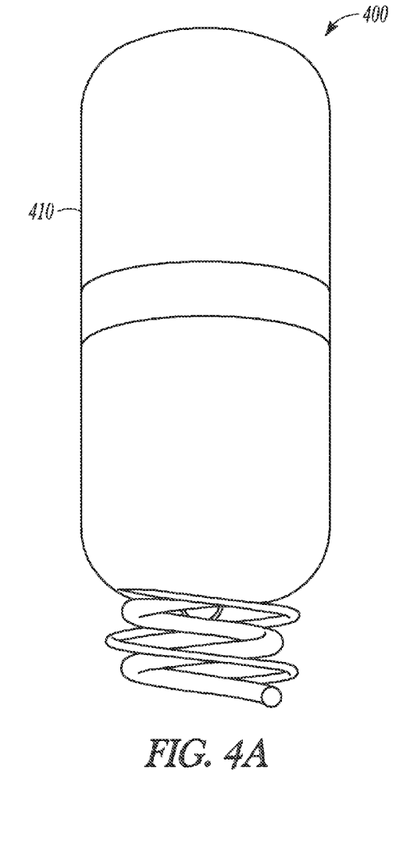
FIGS. 4A-B illustrate examples of an untethered electrostimulator device.
Figure 4B:
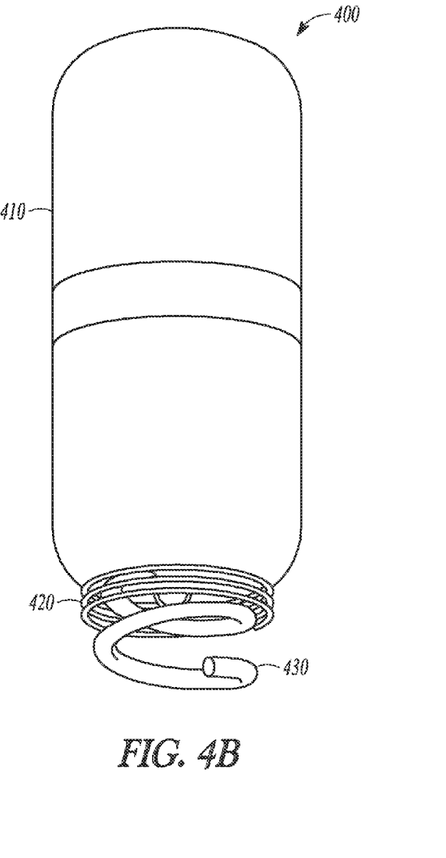

FIGS. 4A-B illustrate examples of an untethered electrostimulator device 400, which can be an embodiment of the implantable apparatus 100. The heart stimulation system 400 can include an untethered electrostimulator device body 410 (e.g., a leadless pacemaker), a primary fixation member 420, and a secondary fixation member 430. FIG. 4A illustrates an example when the primary and secondary fixation members are in their respective disengaged state (i.e., without engaging with the target tissue); and FIG. 4B illustrates an example of the primary and the secondary fixation members when at least a portion of the primary or the secondary fixation member is engaged with the heart tissue.

The untethered electrostimulator device body 410 can be configured to locally generate and locally deliver electrostimulation to the heart or other stimulation site such as to achieve one or more therapeutic effects, such as chronic bradycardia pacing, tachycardia pacing, cardioversion or defibrillation shock, or cardiac resynchronized pacing such as for treating congestive heart failure. The untethered electrostimulator device body 410 can include circuitry, instructions (e.g., software or firmware), and a battery or other power source or storage device, or one or more other electrical components or functional modules. In some examples, the circuitry in the untethered electrostimulator device body 410 can be configured to sense and analyze one or more biopotential signals from the heart, such as one or more intrinsic electrical signals obtained from the heart using the electrodes such as before or in response to the electrostimulation to the heart, or other physiological signals. The housing of the untethered electrostimulator device body 410 can be made of one or more biocompatible materials, such as titanium or a titanium alloy.

The primary fixation member 420 and the secondary fixation member 430, as discussed in FIGS. 2A-B and FIGS. 3A-B, can include respective helical coils coaxially attached to an exterior surface of the untethered electrostimulator device body 410, thereby forming a dual-helix structure. Both the primary and secondary fixation members can axially align with the electrostimulator device body 410. The primary fixation member 420 can include an active fixation mechanism such as a tapered end, a hook, a barb, or other sharpened structure such as on the distal end of or along the helical coil. The secondary fixation member 430 can be configured to be collapsed and compressed to bias against, and without being actively engaged or affixed to the stimulation site of the heart, when the primary fixation member 420 is engaged or affixed to the heart. The secondary fixation member 430 can be made out of more pliant material and having a diameter greater than the primary fixation element 420. For example, at least a portion of the secondary fixation member 430 can include one or more of stainless steel, titanium alloy, plastic, polyurethane, polymer, ceramic, other synthetic biocompatible metallic or non-metallic materials, or a combination of two or more materials such as plastic-coated metal, or multifilar windings around the flexible metallic core. In various examples, the secondary fixation member 430 can include anti-unscrewing features that prevent the primary fixation member 420 from unwinding from the target tissue. Examples of the anti-unscrewing features of the secondary fixation member 430 can include a helical coil with an opposite handedness than the primary fixation member 420, blunted distal terminal on the helical coil, a textured or porous processing or a coating of porous biomaterial or porous synthesized material of helical coil for promoting tissue ingrowth, among other features.

As in the elongated medical device 300 discussed in FIGS. 3A-C, the untethered electrostimulator device body 410 can include one or more electrodes located such as on the exterior of the untethered electrostimulator device 410. In some examples, one or both of the primary and the secondary fixation members can be electrically coupled to the circuitry in the untethered electrostimulator device body 410 to deliver the electrostimulation to the heart. The untethered electrostimulator device 410 can be configured to deliver a unipolar stimulation such as using the primary fixation member 420, and using a return electrode such as a housing or "can" of the untethered electrostimulator device 420. A bi-polar stimulation can be provided such as between the primary fixation member 420 and the secondary fixation member 430 or a separate electrode on the exterior surface of untethered electrostimulator device body 410.

In some embodiments, the heart stimulation system 400 can include a separate fixation tool used for assist the fixation of the untethered electrostimulator device body 410. The fixation tool, when used with the untethered electrostimulator device body 410, can be configured to be used, such as by an end user, to hold and deliver the untethered electrostimulator device body 410 to or near the stimulation site, and engage the primary and secondary fixation members to the target tissue. For example, the fixation tool can have an elongated body that enables an end user to operate, such as from a proximal end of the fixation tool, on the fixation tool. The untethered electrostimulator device body 410 can have a first coupler feature sized, shaped, or otherwise configured to be coupled to a second coupler feature on the fixation tool, such that the fixation tool can be securely attached to the untethered electrostimulator device body 410. The first coupler feature of the untethered electrostimulator device body 410 and the second coupler feature on the fixation tool can also be configured to be detached from each other, such as by an end user, after the untethered electrostimulator device body 410 has been securely affixed. Examples of the coupler features can include one or more of a snap-fit coupling, a rotation or a screwing-in coupling, a slide-in engagement, or one or more other locking mechanisms.

Figure 5:
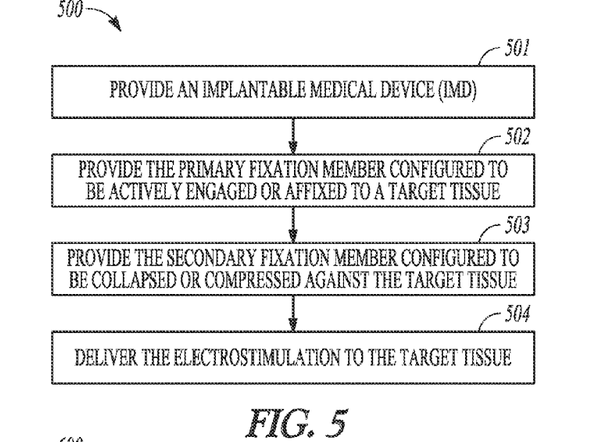
FIG. 5 illustrates an example of a method for stimulating a target issue.

FIG. 5 illustrates an example of a method 500 for stimulating a target issue in a body, such as using one or more of the implantable medical device 300 (such as an implantable lead, a catheter, or other therapy delivery devices) or the untethered electrostimulator device 400.

At 501, an implantable medical device (IMD) is provided for use to stimulate a stimulation site such as to achieve a desired diagnostic or therapeutic effect. For example, the stimulation can be delivered to an exterior or an interior of a heart for treating heart rhythm disorders or for improving the cardiac function such as in patients with congestive heart failure (CHF). Examples of the electrostimulation for such purposes can include temporary or chronic bradycardia pacing, tachycardia pacing, cardioversion or defibrillation shock, or cardiac resynchronized pacing such as for treating CHF. In various examples, the IMD can be configured to deliver electrostimulation to other tissues or organs including an interior or exterior of an artery or vein, a nerve bundle, skin, a carotid body, a stomach or intestine, a bladder, a kidney, soft tissues, gastric tissues, or neural tissues.

In an example, providing the IMD includes providing an implantable lead (such as the elongated implantable device 300), placing and positioning it to the stimulation site, and engaging or affixing the implantable lead to the target tissue. The implantable lead can have an elongated lead body extended between a proximal end and a distal end. The proximal end can be configured to be coupled to an electrostimulator device such as an ambulatory medical device, a PSA circuit, or a bedside medical device. The distal end can be configured to be attached to one or more stimulation electrodes to provide the capability of electrostimulation.

In another example, providing the IMD includes providing an untethered electrostimulator device to be engaged or affixed to the target tissue. The untethered electrostimulator can include a housing or a "can" including an electrostimulation circuitry configured to be coupled to one or more electrodes, such as on the exterior surface of the untethered electrostimulator device, to provide the capability of electrostimulation of the target tissue.

At 502, a primary fixation member is provided for use to affix the IMD to the desired site on the target tissue for electrostimulation. The primary fixation member can be configured to be actively engaged or affixed to a target tissue, such as by using a screw-in helical or spiral coil as illustrated in FIGS. 2A-B, 3A-B, and 4A-B, or other rotationally-oriented active fixation element. The method includes rotating the primary fixation member directly or indirectly such as to engage the rotationally-oriented fixation element to the target tissue. Direct rotation of the primary fixation member can include directly rotating, such as by an end user, the IMD that is attached to the primary fixation member. Indirect rotation of the primary fixation member can include coupling the IMD to a fixation tool such as through one or more coupler features on the IMD.

At 503, a secondary fixation member can be provided such that when at least a portion of the primary fixation member is affixed to the target tissue, the secondary fixation member can be configured to be collapsed or compressed against the target tissue but not to actively affix to the desired stimulation site. In an example, the secondary fixation member can have a shorter exposed length than the primary fixation member. The collapsing or compression of the secondary fixation member between the IMD and the target tissue can be achieved such as when the primary fixation member is rotated into the target tissue. By causing a collapsing or compression of the secondary fixation member between the IMD and the target tissue, an increased tension between the primary fixation member and the engaged tissue can be achieved. In some examples, the secondary fixation member can include a helical coil with a reversed handedness than the helical coil of the primary fixation member. The opposite handedness can allow the secondary fixation member to be effectively compressed without actively penetrating or damaging the tissue. The opposite handedness can also offer an anti-unscrewing feature. The compression force exerted against the target tissue and the reverse handedness can reduce the likelihood of unwinding or other means of dislodgment of the primary fixation member from the target tissue, such as due to heart beat or patient motion or activity over time.

When the primary fixation member is securely engaged to the target tissue and the secondary fixation member compressed against the tissue, electrostimulation can be delivered to the target tissue at 504. The IMD, such as an implantable lead or an untethered electrostimulator device, can include one or more electrodes electrically coupled to an electrostimulation generator circuit which can provide and deliver electrostimulation to the target tissue via the one or more electrodes. The electrostimulation generation circuit can be located in a separate electrostimulator device configured to mechanically and electrically coupled to the implantable lead, or can be located in the untethered electrostimulator device. The electrostimulation electrode can be secured using at least one of the primary or the secondary fixation member. In some examples, the primary or the secondary fixation members can be electrically connected to the electrostimulation generation circuit and deliver electrostimulation to the target tissue from the respective fixation members.

Figure 6:
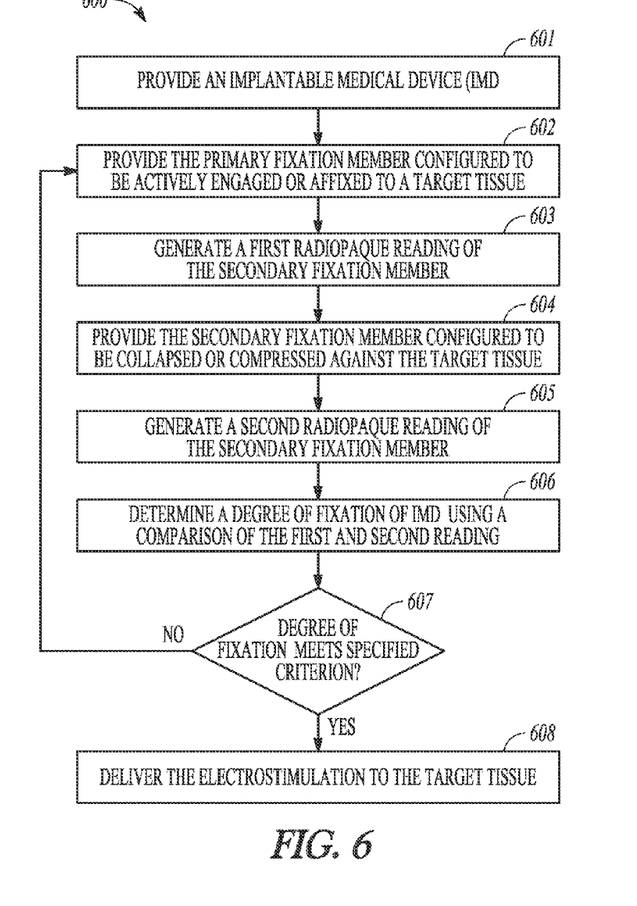
FIG. 6 illustrates an example of a method for stimulating a target issue.

FIG. 6 illustrates an example of a method 600 for stimulating a target issue in a body using information about degree of fixation of the implantable medical device. The electrostimulation can be achieved such as using one or more of the implantable medical device 300 (such as an implantable lead, a catheter, or other therapy delivery devices) or the untethered electrostimulator device 400.

An implantable medical device (IMD), such as an implantable medical lead or an untethered electrostimulator device, can be provided at 601. At 602, a primary fixation member, such as a tapered, a hooked, or a screw-in helical coil, can be provided on the IMD for use to affix the IMD to the target stimulation site.

At 603, a first radiopaque reading of a secondary fixation member can be obtained before it gets compressed or deformed otherwise in response to the primary fixation member being actively engaged to the tissue. As discussed in FIG. 5, the secondary fixation element can be configured to be collapsed or compressed against the target tissue but not to actively affix to the desired stimulation site. A radiopaque reading of the secondary fixation member can be used to determine the degree of compression against the tissue. For example, the secondary fixation member can be coated with radiopaque material such as dense metal powders and compounds including one or more of barium, barium sulfate, tungsten, bismuth compounds, among other substances opaque to x-rays. The first radiopaque reading can include, for example, one or more x-ray images or fluoroscopic images, or a qualitative depiction or a quantitative measurement of a length or other morphological characteristics of the secondary fixation member.

At 604, the secondary fixation member can be collapsed and compressed against the target tissue. The collapsing or compression can be achieved such as when the primary fixation member is rotated into the target tissue. While the primary fixation member is being engaged to the tissue, a second radiopaque reading of the secondary fixation member can be obtained at 605. The second radiopaque reading can include, for example, one or more x-ray images or fluoroscopic images of the secondary fixation member. In an example, the second radiopaque reading of the secondary fixation member at 605 can be taken under a specified condition comparable to that when the first radiopaque reading is taken at 603, including one or more of a viewing angle, a magnification mode, or other settings for use to obtain the images. A qualitative or a quantitative parameter, such as the length or other morphological characteristics of the secondary fixation member, can be determined from the second radiopaque reading.

A degree of fixation of the IMD onto the tissue can be determined at 606, such as by using a comparison of the first and the second radiopaque readings of the secondary fixation member. One or both readings can be presented to an end user such as a physician. To determine if the IMD has been desirably affixed to the target tissue, a parameter indicative of degree of deformation of the secondary fixation member can be computed. The deformation parameter can include, for example, a difference, ratio, or other relative measures between the length of the helical coil of the secondary fixation member as shown in the first and second radiopaque readings.

In some embodiments, a radiopaque reading of both the primary and the secondary fixation members can be obtained prior to affixing the primary fixation element to the tissue at 603 and after at least a portion of the primary fixation element has been engaged with the tissue at 605. The degree of fixation of IMD can be determined at 606 using the degree of engagement of the primary fixation member with the target tissue and the degree of compression of the secondary fixation member against the target tissue.

At 607, the degree of fixation as determined in 606 can be compared to a specified criterion. Examples of the criterion can include a threshold value or a specified range of values for the degree of fixation, such as a threshold or range of the length of compression of the helical coil of the secondary fixation member. If the degree of fixation does not meet the specified criterion, then the primary fixation member can be further engaged to the target tissue at 602. If the degree of fixation meets the specified criterion, then the IMD is deemed properly and securely affixed to the target tissue, and the programmed electrostimulation can be delivered to the target tissue.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An implantable apparatus comprising:
   an electrostimulation electrode assembly including:
      a primary fixation member that is sized, shaped, or configured to be actively engaged or affixed to a target tissue of a patient;
      a secondary fixation member that is sized, shaped, or configured to passively bias against the target tissue when the primary fixation member is engaged or affixed to the target tissue; and
      an electrostimulation electrode body having a proximal end and a distal end, the electrode body including at least one electrode, wherein the electrode body is sized, shaped, or configured to be attached to the primary fixation member and the secondary fixation member, and to deliver electrostimulation to a stimulation site of the patient via the at least one electrode;
      wherein the primary fixation member and the secondary fixation member extend distally from the distal end of the electrode body;

wherein the secondary fixation member includes an expanded configuration and a collapsed configuration;
wherein the secondary fixation member extends distally a first distance when in the expanded configuration;
wherein the secondary fixation member extends distally a second distance when in the collapsed configuration; and
wherein the first distance is greater than the second distance.

2. The apparatus of claim 1, wherein:
the primary fixation member includes a first helical element; the secondary fixation member includes a second helical element; and
the first and second helical elements are coaxial.

3. The apparatus of claim 2, wherein the first helical element includes a screw-in helix first coil with at least one of a first handedness or a first pitch, and the second helical element includes a second coil with at least one of a second handedness or a second pitch, the at least one of the first handedness or the first pitch being non-identical to the respective the at least one of the second handedness or the second pitch.

4. The apparatus of claim 2, wherein the first helical element extends farther from the electrostimulation electrode body than the second helical element.

5. The apparatus of claim 1, wherein the primary fixation member is stiffer than the secondary fixation member.

6. The apparatus of claim 1, wherein at least a portion of the secondary fixation member is a polymer.

7. The apparatus of claim 1, wherein the secondary fixation member includes radiopaque material such that the secondary fixation member is capable of providing a radiopaque reading of a degree of fixation of the electrostimulation electrode assembly.

8. The apparatus of claim 1, wherein the electrostimulation electrode body comprises an elongated wire extending between a distal end and a proximal end, the proximal end being configured to be coupled to a separate electrostimulation generator configured to generate electrostimulation to be delivered to the stimulation site.

9. The apparatus of claim 1, wherein the electrostimulation electrode body comprises a housing that includes an electrostimulation generation circuit configured to generate and deliver electrostimulation to the stimulation site.

10. The apparatus of claim 9, wherein the electrostimulation generation circuit is configured to be electrically coupled to at least one of the primary fixation member or the secondary fixation member, the at least one of the primary fixation member or the secondary fixation member configured to provide an electrode for delivering chronic electrostimulation to the target tissue.

11. An implantable medical device (IMD), comprising:
a primary fixation member that is sized, shaped, or configured to be actively engaged or affixed to a heart;
a secondary fixation member that is sized, shaped, or configured to be collapsed and compressed to passively bias against, and without being actively engaged or affixed to, the heart when the primary fixation member is engaged or affixed to the heart; and
an electrostimulation unit that is sized, shaped, or configured to be attached to the primary fixation member and the secondary fixation member, and that includes at least one electrode to deliver electrostimulation to a stimulation site of the heart when at least one of a primary or the secondary fixation member is engaged with the heart;
wherein the primary fixation member and the secondary fixation member extend distally from the distal end of the electrode electrostimulation unit;
wherein the secondary fixation member includes an expanded configuration and a collapsed configuration;
wherein the secondary fixation member extends distally a first distance when in the expanded configuration;
wherein the secondary fixation member extends distally a second distance when in the collapsed configuration; and
wherein the first distance is greater than the second distance.

12. The device of claim 11, wherein the electrostimulation unit comprises an elongated wire extending between a distal end and a proximal end, the proximal end configured to be coupled to an electrostimulation generator, and the distal end configured to be attached to the at least one of the primary and the secondary fixation members.

13. The device of claim 11, wherein the electrostimulation unit comprises a housing including a stimulation circuit configured to generate and deliver an electrostimulation to the stimulation site of the heart through the at least one of the primary or the secondary fixation member.

14. A method comprising:
providing an implantable medical device (IMD) configured to deliver an electrostimulation to a stimulation site of a patient;
providing the IMD to be engaged or affixed to a target tissue, including:
providing a primary fixation member configured to be actively engaged or affixed to the target tissue; and
rotating the primary fixation member to engage the target tissue; and
providing a secondary fixation member configured to be passively collapsed or compressed against the tissue when the primary fixation member is engaged or affixed to the target tissue; and
delivering the electrostimulation to the target tissue via at least one electrode;
wherein the primary fixation member and the secondary fixation member extend distally from the distal end of the electrode;
wherein the secondary fixation member includes an expanded configuration and a collapsed configuration;
wherein the secondary fixation member extends distally a first distance when in the expanded configuration;
wherein the secondary fixation member extends distally a second distance when in the collapsed configuration; and
wherein the first distance is greater than the second distance.

15. The method of claim 14, wherein providing the IMD to be engaged or affixed to the target tissue includes determining a degree of fixation of the IMD when at least one of the primary or the secondary fixation member is engaged or affixed to the target tissue.

16. The method of claim 15, wherein determining the degree of fixation includes:
generating a first radiopaque reading of the secondary fixation member before being collapsed or compressed against the target tissue;
generating a second radiopaque reading of the secondary fixation member after being collapsed or compressed against the target tissue; and determining a degree of deformation of the secondary fixation member using a comparison between the first radiopaque reading and the second radiopaque reading.

17. The method of claim 14, wherein:

providing the IMD includes providing an implantable lead to be engaged or affixed to the target tissue, the implantable lead including a proximal end configured to be coupled to an electrostimulator device and a distal end configured to be attached to the primary fixation member and the secondary fixation member; and delivering the electrostimulation includes configuring the electrostimulator device for delivering electrostimulation via the implantable lead to an electrostimulation electrode secured using at least one of the primary or the secondary fixation member.

18. The method of claim 14, wherein:

providing the IMD includes providing an untethered electrostimulator device to be engaged or affixed to the target tissue, the untethered electrostimulator including a housing configured to be attached to the primary fixation member and the secondary fixation member; and delivering the electrostimulation includes configuring the untethered electrostimulator for delivering an electrostimulation to an electrostimulation electrode secured using at least one of the primary or the secondary fixation member.

\* \* \* \* \*